(12) United States Patent
Huck et al.

(10) Patent No.: US 11,234,662 B2
(45) Date of Patent: Feb. 1, 2022

(54) METHOD AND DEVICE FOR CHANGING THE SPATIAL INTENSITY DISTRIBUTION OF AN X-RAY BEAM

(71) Applicant: Siemens Healthcare GmbH, Erlangen (DE)

(72) Inventors: Sascha Manuel Huck, Bubenreuth (DE); Karl Stierstorfer, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/971,077

(22) PCT Filed: Nov. 29, 2018

(86) PCT No.: PCT/EP2018/082953
§ 371 (c)(1),
(2) Date: Aug. 19, 2020

(87) PCT Pub. No.: WO2019/161953
PCT Pub. Date: Aug. 29, 2019

(65) Prior Publication Data
US 2021/0100516 A1    Apr. 8, 2021

(30) Foreign Application Priority Data

Feb. 26, 2018  (DE) .................... 10 2018 202 876.1
Aug. 24, 2018  (DE) .................... 10 2018 214 311.0

(51) Int. Cl.
*A61B 6/00*    (2006.01)
*A61B 6/03*    (2006.01)
*A61B 6/02*    (2006.01)

(52) U.S. Cl.
CPC ............ *A61B 6/4035* (2013.01); *A61B 6/025* (2013.01); *A61B 6/032* (2013.01)

(58) Field of Classification Search
CPC ....... A61B 6/4035; A61B 6/025; A61B 6/032; A61B 6/06; G21K 1/10; A61N 5/1045; A61N 2005/1095
See application file for complete search history.

(56) References Cited

U.S. PATENT DOCUMENTS 4,622,625 A * 11/1986 Becker .................... F21V 14/04
                                                    362/297
5,029,332 A    7/1991 Nakazawa
(Continued)

FOREIGN PATENT DOCUMENTS

| DE | 102016213990 A1 | 9/2017 |
|---|---|---|
| EP | 3217408 A2 | 9/2017 |
| FR | 2485790 A1 | 12/1981 |

OTHER PUBLICATIONS

International Search Report for International Application PCT/EP2018/082953 dated Mar. 4, 2019.

*Primary Examiner* — Courtney D Thomas
(74) *Attorney, Agent, or Firm* — Harness, Dickey & Pierce, P.L.C.

(57) ABSTRACT

A method is for changing a spatial intensity distribution of an x-ray beam. In an embodiment, the method includes generating an x-ray beam by an x-ray source; guiding a beam path of the x-ray beam through a form filter with a plurality of lamellas, the form filter including a holder apparatus and the plurality of lamellas being arranged in the holder apparatus such that each lamella has at least one straight line running through the respective lamella in parallel to the further lamellas. The method further includes aligning the plurality of lamellas relative to the beam path by controlled movement of at least one part of the plurality of lamellas relative to one another and thereby changing the spatial intensity distribution of the x-ray beam. An apparatus, configured to carry out such a method, an irradiation (Continued)

arrangement and a medical imaging apparatus are further disclosed.

25 Claims, 11 Drawing Sheets

(56) References Cited

U.S. PATENT DOCUMENTS

| | | |
|---|---|---|
| 7,403,597 B2 | 7/2008 | Raupach |
| 8,218,721 B2 | 7/2012 | Raupach et al. |
| 8,873,704 B2 | 10/2014 | Stierstorfer |
| 2010/0008472 A1 | 1/2010 | Bohn et al. |
| 2010/0053208 A1 | 3/2010 | Menningen et al. |
| 2017/0011815 A1 | 1/2017 | Pack et al. |
| 2018/0033514 A1 | 2/2018 | Stierstorfer |

* cited by examiner

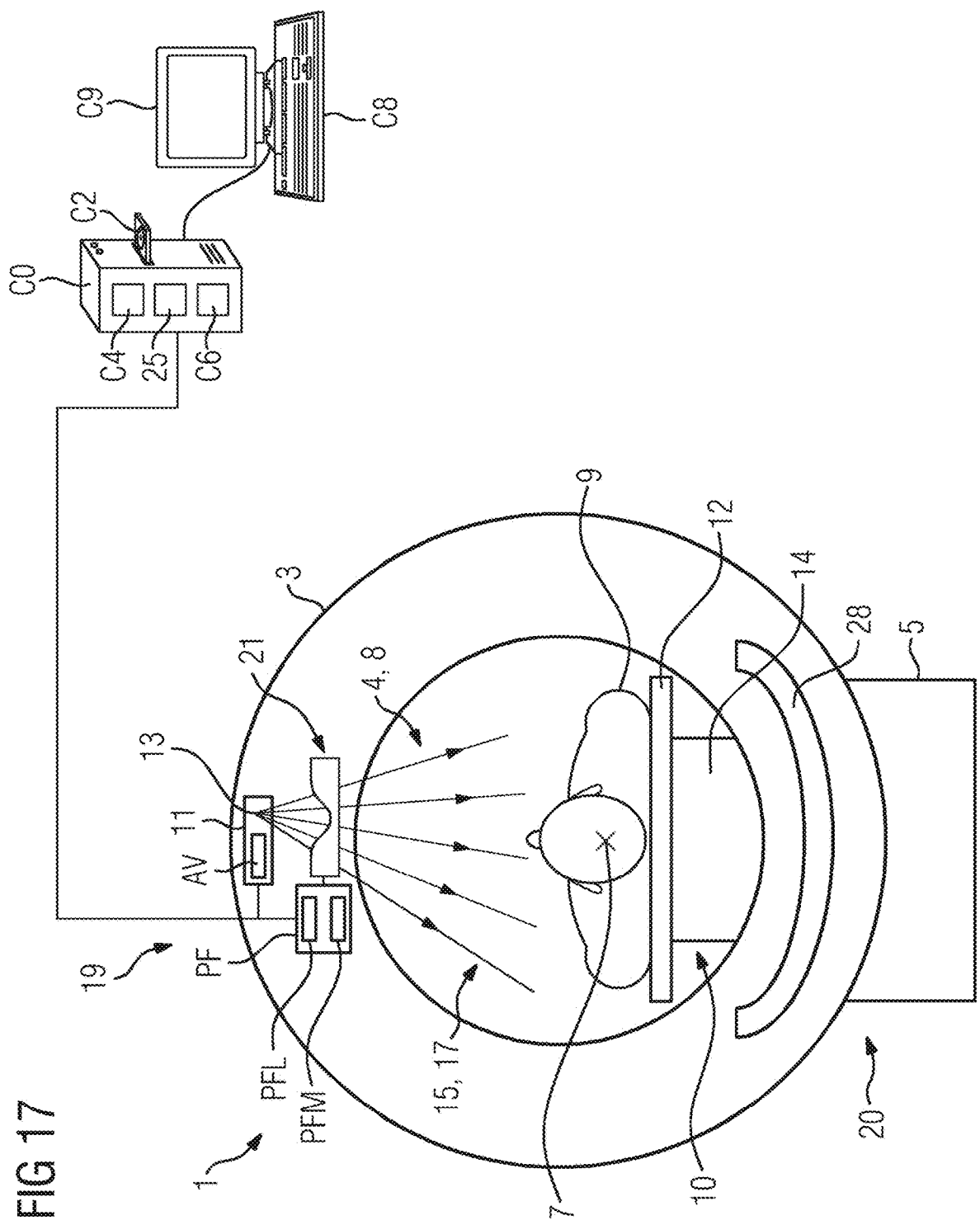

METHOD AND DEVICE FOR CHANGING THE SPATIAL INTENSITY DISTRIBUTION OF AN X-RAY BEAM

PRIORITY STATEMENT

This application is the national phase under 35 U.S.C. § 371 of PCT International Application No. PCT/EP2018/082953 which has an International filing date of Nov. 29, 2018, which designated the United States of America and which claims priority to German patent application numbers 102018202876.1 filed Feb. 26, 2018 and 102018214311.0 filed Aug. 24, 2018, the entire contents of all which are hereby incorporated herein by reference.

FIELD

Embodiments of the present application generally relate to a method for changing a spatial intensity distribution of an x-ray beam; to an apparatus for changing a spatial intensity distribution of an x-ray beam, further to an irradiation arrangement and a medical imaging apparatus; and to a computed tomography device.

BACKGROUND

In x-ray imaging and thus in a Computed Tomography device (CT device), the x-ray radiation used is generated by an x-ray source. In this case the x-ray source mostly corresponds to an x-ray tube. From a generation point of the x-ray radiation in the x-ray tube assumed to be punctiform in relation to the dimensions of the imaging facility the beam path essentially fans out radially, wherein the spatial angular range in which any emission at all of the x-ray beam takes place can be influenced or restricted by the geometry of the anode of the x-ray tube and possibly by a subsequent diaphragm arrangement.

In a CT device the x-ray tube is arranged on a rotating ring which, when the CT device is operating, carries out a rotational movement about an axis along which the region of the body of a patient to be imaged is positioned. This axis is generally referred to by the person skilled in the art as the system axis of the CT device. The beam path of the x-ray tube is now, possibly with the assistance of corresponding diaphragms, directed in the shape of a fan from the generation point into the interior space surrounded by the rotating ring.

For a contrast and image resolution by the CT device that is as high as possible an intensity of the x-ray radiation that is as high as possible is desirable. On the other hand however, for medical reasons, this radiation intensity is to be restricted at least over an average time for a given region of the body. In order to use the dose applied to a patient by the radiation as effectively as possible it can be advantageous for example to be able to change the spatial intensity distribution of the x-ray beam dynamically as a function of physiological and/or anatomical parameters of the patient. For example account can be taken in this way during a rotation of the x-ray source about the patient that radiation striking the front of the patient covers a significantly shorter distance through the patient, and consequently experiences a much lower absorption than radiation striking the side of the patient, which propagates from one shoulder to the opposite shoulder for example. It can also be advantageous to be able to set the intensity distribution in particular for taking account of regions-of-interest (ROI) in the imaging method very locally and flexibly within the irradiated area.

Thus in a computed tomography examination of a patient the dose distribution can be optimized in respect of dose and noise by the intensity distribution of x-ray radiation being changed during the acquisition of projection data. In conventional computed tomography devices form filters, which are permanently built into the beam path of the x-ray radiation for example or can be moved into the beam path of the x-ray radiation if required, are used to form the dose profile. These form filters are as a rule not suitable for changing the dose profile during the ongoing acquisition process.

U.S. Pat. No. 7,403,597 B2 discloses a diaphragm apparatus for an x-ray facility intended for scanning an object.

U.S. Pat. No. 8,218,721 B2 discloses a diaphragm for explicit influencing of x-ray radiation that emanates from an x-ray focus of a CT device and serves to scan an examination object.

U.S. Pat. No. 8,873,704 B2 discloses a filter for an x-ray facility for shaping an intensity profile of an x-ray radiation emanating from an x-ray source.

DE 10 2016 213 990 A1 discloses a method for setting a spatial intensity distribution of an x-ray beam and an apparatus comprising a filter with a plurality of lamella blades for carrying out the method.

US 2017/0011815 A1 discloses an x-ray filter arrangement, comprising a plurality of x-ray attenuating layers that are arranged in a stack, wherein the x-ray attenuating layers are arranged at an angle to one another in order to have a focus point.

US 2018/0033514 A1 discloses a method for setting a spatial intensity distribution of an x-ray beam, wherein an x-ray beam is generated and a beam path of the x-ray beam is guided in a direction of propagation by a form filter including a plurality of lamella plates. The lamella plates are made of a strongly absorbent material and are embodied as very narrow, planar parts. When the lamella are aligned to the focus the attenuation of the x-ray radiation is small, since only the part of the x-ray radiation that strikes the narrow side of the lamella is absorbed into the lamella. By defocusing an attenuation profile can be set by the surface on which the x-ray beam interacts with the lamella being enlarged.

SUMMARY

Embodiments of the invention specify an improved method and an improved apparatus for changing a spatial intensity distribution of an x-ray beam.

Embodiments that are advantageous and seen as inventive in or of themselves are the subject matter of the claims and the description given below.

At least one embodiment of the invention relates to a method for changing a spatial intensity distribution of an x-ray beam, comprising:

generation of an x-ray beam by an x-ray source;

guidance of a beam path of the x-ray beam by a form filter with a plurality of lamellas, wherein the form filter has a holder apparatus and wherein the plurality of lamellas are arranged in the holder apparatus in such a way that each lamella has at least one straight line running through the respective lamella in parallel to the further lamellas; and alignment of the plurality of lamellas relative to the beam path by controlled movement of at least a part of the plurality of lamellas relative to one another and thereby making a change to the spatial intensity distribution of the x-ray beam.

At least one embodiment of the invention further relates to an apparatus for changing a spatial intensity distribution of an x-ray beam, comprising:

a form filter, which is able to be introduced into a beam path of an x-ray beam generated by an x-ray source, wherein the form filter comprises a holder apparatus in which a plurality of lamellas are arranged, wherein each lamella of the plurality of lamellas has a straight line running through the respective lamella in parallel to the further lamellas and the plurality of lamellas are able to be aligned relative to the beam path by a controlled movement of at least a part of the plurality of lamellas relative to one another; and a control unit, which is embodied to control the controlled movement of the part of the plurality of lamellas and thereby to change the spatial intensity distribution of the x-ray beam.

At least one embodiment of the invention further relates to an irradiation arrangement, comprising:

an x-ray source for generation of the x-ray beam; and an embodiment of the inventive apparatus disclosed, wherein the apparatus is positioned in a position relative to the x-ray source.

At least one embodiment of the invention further relates to a medical imaging apparatus, having an inventive irradiation arrangement of at least one embodiment.

At least one embodiment of the invention further relates to an inventive medical imaging apparatus, wherein the medical imaging apparatus is a computed tomography device.

At least one embodiment of the invention further relates to an apparatus for changing a spatial intensity distribution of an x-ray beam, comprising:

a form filter, which is able to be introduced into a beam path of an x-ray beam generated by an x-ray source, wherein the form filter has a holder apparatus, in which a plurality of lamellas are arranged, wherein each lamella of the plurality of lamellas has at least one straight line running through the respective lamella in parallel to the further lamellas and further has a height profile in a plane defined by the respective lamella, wherein the height profile relates to a height of the respective lamella, which extends at right angles to the straight line running through the respective lamella and changes along the straight line running through the respective lamella; and a control unit, which is embodied to control a controlled movement of the form filter relative to the x-ray source and/or a controlled movement of lamellas of at least a part of the plurality of lamellas relative to one another and thereby to change the spatial intensity distribution of the x-ray beam.

At least one embodiment of the invention further relates to a computed tomography device, comprising:

an x-ray source and an x-ray detector which interacts with the x-ray source, wherein the x-ray source and the x-ray detector are arranged about a system axis of the computed tomography device, which is located rotatably between the x-ray source and the x-ray detector; and an apparatus for changing a spatial intensity distribution of an x-ray beam of an embodiment of one of the disclosed aspects, wherein the form filter is arranged between the x-ray source and the system axis.

BRIEF DESCRIPTION OF THE DRAWINGS

The invention will be explained below on the basis of forms of embodiment that refer to the enclosed figures. The presentation in the figures is schematic, greatly simplified and not necessarily true-to-scale.

In the figures:

FIG. 17 shows a schematic view of a computed tomography device.

DETAILED DESCRIPTION OF THE EXAMPLE EMBODIMENTS

Figure 1:
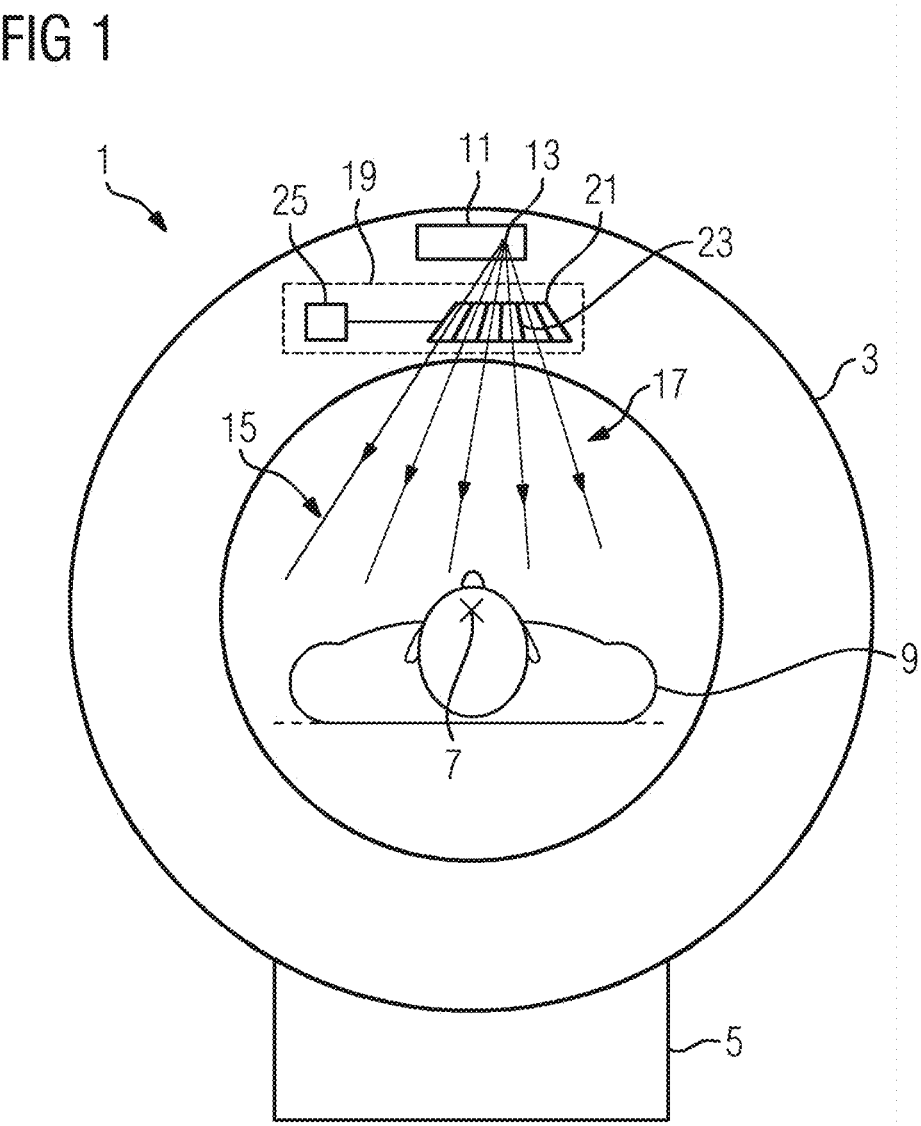
FIG. 1 shows a schematic view of a medical imaging apparatus.

At least one embodiment of the invention relates to a method for changing a spatial intensity distribution of an x-ray beam, comprising:

generation of an x-ray beam by an x-ray source;

guidance of a beam path of the x-ray beam by a form filter with a plurality of lamellas, wherein the form filter has a holder apparatus and wherein the plurality of lamellas are arranged in the holder apparatus in such a way that each lamella has at least one straight line running through the respective lamella in parallel to the further lamellas; and alignment of the plurality of lamellas relative to the beam path by controlled movement of at least a part of the plurality of lamellas relative to one another and thereby making a change to the spatial intensity distribution of the x-ray beam.

A spatial intensity distribution of the x-ray beam here is to be understood in particular as the distribution of the intensity of the x-ray beam in the direction of propagation.

The direction of propagation of the x-ray beam can still be restricted before it reaches the form filter by a number of diaphragms, for example into a fan shape.

For example the spatial intensity distribution can be evenly distributed over the entire irradiated region, meaning i.e. to have a constant intensity profile, or the irradiated region can have part regions with higher and lower intensity, i.e. a radiation profile with varying intensity.

A lamella is in particular to be understood as a component embodied as a planar component.

The lamellas in this case can be embodied flat or have a curvature along at least one of the two local surface directions. The embodiment of the lamellas in width, length and height can be freely selected in wide ranges and can also vary within a lamella for example. A combination of differently embodied lamellas is also possible for example.

The material from which the lamellas are manufactured can be freely selected within a wide range, in particular in as far as it is firm enough to be held with a stable shape in the holder apparatus. When an x-ray beam strikes it the lamella material absorbs the intensity of the x-ray beam. Through the absorption by the lamella material the spatial intensity distribution of the x-ray beam can primarily be changed by the geometry of the lamellas set in the form filter. Preferably the lamellas have strongly absorbent materials, for example tungsten and/or a tungsten alloy. This enables any scattered radiation occurring and a spectral beam hardening of the x-ray beam to be minimized.

The plurality of lamellas is arranged in a holder apparatus. The holder apparatus can in particular involve an individual component or an assembly. In particular the holder apparatus can have a through-opening that is facing towards the x-ray source. For example the through-opening is rectangular, but it can also be a different shape, for example elliptical. The holder apparatus can comprise plastic and/or metal. For example the holder apparatus is made of aluminum. In particular the holder apparatus can be arranged fixed in the form filter, meaning that it cannot be moved.

In particular the plurality of lamellas is arranged within the opening in the holder apparatus in such a way that each lamella has at least one straight line running through it that runs in parallel to the further lamellas. In particular the group of parallel straight lines through the plurality of lamellas can lie in one plane, which stands at right angles to a central axis of the x-ray beam. The group of parallel straight lines can thus be described for example as a flat, grating-like structure in relation to the central axis of the x-ray beam. For example a long edge of each lamella corresponds in each case to one straight line of the parallel group of straight lines. Straight lines to the sides of the respective long edges of the lamellas are also possible however.

The distance between the parallel straight edges of the lamellas arranged in the form filter can be freely selected over a wide range. Thus for example different grid ratios for the opening between two adjacent lamellas, different line frequencies or also combinations can be realized within a form filter.

In particular the plurality of lamellas arranged in the holder apparatus can comprise lamellas arranged both movably and also immovably, wherein the spatial intensity distribution is changed via the movement of at least a part of the lamellas arranged movably. For example a lamella can be attached immovably in the holder apparatus, which starting from the x-ray beam propagating largely radially or in a fan shape, is positioned in the central beam axis of the x-ray beam and divides the form filter into two areas to the side of the central axis, which can be aligned independently of one another.

The movement of the part of the plurality of lamellas is achieved by a controlled movement, wherein the lamellas can be explicitly positioned relative to one another and thus relative to the beam path of the x-ray beam.

The controlled explicit movement of the lamellas in relation to one another in particular also does not exclude a uniform movement of the part plurality of lamellas in the form filter.

The spatial intensity distribution can be changed by the absorption of parts of the x-ray beam by the material of the lamellas. An x-ray beam that propagates largely in parallel to a lamella will in any case strike the lamella in a negligibly small end-face edge and the lamella will scarcely influence the spatial intensity distribution of the x-ray beam beyond the lamella.

If the planar side of the lamella does not run in parallel locally to the beam path, but has a non-disappearing normal component by comparison with this, a part of the intensity of the x-ray beam is absorbed and the spatial intensity distribution beyond the lamella is changed.

For example the lamellas of the plurality of lamellas can be aligned in such a way that the lamellas run to a focus point, that at least one straight line running through the respective lamella exists for each of the lamellas, which is aligned to the focus point. If the beam path of an x-ray beam, of which the intensity profile is now to be changed via the form filter, is now guided so that the x-ray beam propagates from the focus point of the form filter largely radially or in a fan shape, then no appreciable attenuation of the intensity of the x-ray beam is achieved by the form filter. In this alignment of the plurality of lamellas in the form filter a maximum intensity of the spatial intensity distribution of the x-ray beam can be generated after its passage through the form filter.

For example at least a few lamellas can be moved out of the position running to the focus point, which leads to an attenuation of the intensity of the x-ray beam in this region and thus to a change of the spatial intensity distribution.

In particular for example both concave and also convex intensity profiles can be created in this way. In particular this is especially advantageous for taking account of regions-of-interest (ROI) in the imaging method.

For example this enables intensity profiles to be created, which in the central areas of the beam path, i.e. in areas of the central beam axis of the x-ray beam, have a higher intensity than in the edge areas, i.e. to the sides of the central areas of the beam path.

For example radiation profiles can be created, which in the edge areas have a higher intensity than in central areas of the beam path.

In particular radiation profiles can also be created, which have an intensity maximum to the sides of the central areas of the beam path.

In particular a created intensity profile can also have two or more global and/or local intensity maxima and/or minima.

In particular intensity profiles can also be created, which do not have a symmetrical intensity profile with regard to the central beam axis.

However a largely uniform absorption can also be achieved over the entire beam path.

At least one embodiment of the invention advantageously makes it possible, with simple and reliable device(s), to change the spatial intensity distribution of an x-ray beam in a spatial and/or temporally variable manner and to adapt it dynamically to the respective imaging requirements.

Advantageously the holder apparatus does not have to be moved relative to the x-ray source. Advantageously this enables complex mountings to be dispensed with. Advantageously this makes a space-saving fitting with less constructional outlay possible.

Advantageously it is possible with the aid of the invention to change the spatial intensity distribution of the x-ray beam in a short time, for example relative to the duration of one gantry rotation.

According to one variant embodiment of the method the plurality of lamellas can be aligned by the rotation of each lamella of the part of the plurality of lamellas to be moved about an axis of rotation.

This enables the part of the plurality of lamellas, with a fixed distance arrangement of the plurality of lamellas, to be positioned running to both one or also to different focus points/focus lines. The rotational movement makes it possible to control the alignment of the plurality of lamellas precisely and predictably.

For example the axis of rotation of each lamella corresponds to the straight line through the respective lamella running in parallel to the further lamellas. The axis of rotation can however also run to the side of this straight line, for example parallel to the line.

According to a further variant embodiment of the method the plurality of lamellas can be aligned by a translation of each lamella of the part of the plurality of lamellas at right angles to the straight line running through the respective lamella in parallel to the further lamellas.

In this way the distance between adjacent lamellas can be adapted in the form filter. In particular the distance can also be adapted before, during or after operation of the form filter and thus also be selected differently in different operating states of the form filter.

In particular a combination of rotation and translation makes possible a further increased number of adaptation options of the spatial intensity distribution after the x-ray beam has passed through the form filter.

In one variant embodiment of the method each lamella of the part of the plurality of lamellas can be moved independently of the movement of the further lamellas.

This allows the spatial intensity distribution to change very flexibly and independently in all subareas of the form filter.

In a further variant embodiment of the method the part of the plurality of lamellas is connected via at least one connection element to at least one further lamella of the plurality of lamellas and the plurality of lamellas is aligned by a controlled movement of the at least one connection element.

For example all adjacent lamellas can be connected to one another or the plurality of lamellas is subdivided into subsets connected to one another. In particular in such cases the movement of one lamella can affect all connected lamellas or the connected lamellas can only be moved jointly. This makes it possible for example to achieve accumulation of the movements of the connection elements or a common movement of connected lamellas, which can lead to an efficient alignment in terms of time of the totality of lamellas in the form filter.

In particular the connection elements can be positioned outside the radiation field illuminated by the beam path of the x-ray beam, in order not to additionally influence the x-ray flux and to minimize scattered radiation.

At least one embodiment of the invention further relates to an apparatus for changing a spatial intensity distribution of an x-ray beam, comprising:

a form filter, which is able to be introduced into a beam path of an x-ray beam generated by an x-ray source, wherein the form filter comprises a holder apparatus in which a plurality of lamellas are arranged, wherein each lamella of the plurality of lamellas has a straight line running through the respective lamella in parallel to the further lamellas and the plurality of lamellas are able to be aligned relative to the beam path by a controlled movement of at least a part of the plurality of lamellas relative to one another; and a control unit, which is embodied to control the controlled movement of the part of the plurality of lamellas and thereby to change the spatial intensity distribution of the x-ray beam.

The control unit is embodied to control the controlled movement of the lamellas. This movement can be carried out by any suitable device. For example at least one actuator connected to the lamellas in each case can be activated explicitly via the control unit. In particular, via the control unit, the user can change the intensity distribution as required for example individually or according to predetermined presettings, for example for specific examination protocols, by moving at least a part of the plurality of lamellas arranged in the form filter.

In particular the device(s) carrying out the movement, for example actuators connected to the lamellas, can be positioned outside the radiation field illuminated by the beam path of the x-ray beam, in order not to additionally influence the x-ray flux and to minimize scattered radiation.

In one variant embodiment of the apparatus, the holder apparatus has a plurality of pairs of mounting points arranged on opposite sides, wherein each lamella of the part of the plurality of lamellas is arranged in each case so that it can be rotated between the mounting points of a pair of mounting points.

In particular, an arrangement by which the lamellas are able to be rotated over a wide range about an axis of rotation is possible. In particular the axis of rotation can match the straight line running through the respective lamella in parallel to the further lamellas. In particular however the axis of rotation can also run to the side of this straight line, for example in parallel to the line.

For example the lamellas can be supported rotatably via guide pins in the opposite mounting points or can be connected to the pairs of mounting points via articulated joints.

The arrangement of the part of the plurality of lamellas in the pairs of mounting points enables the part of the plurality of lamellas with a fixed distance arrangement between adjacent lamellas to be arranged by a rotation of the lamellas precisely and reliably aligned running to one and also to different focus points. In this way the spatial intensity distribution can be changed precisely and reliably. For example in this way both convex and concave intensity profiles but also other types of intensity profiles can be created.

In one variant embodiment of the apparatus the holder apparatus has a pair of guide rails attached to opposite sides, wherein each lamella of the part of the plurality of lamellas is arranged via guide pins in the pair of guide rails and is arranged so that it can be moved in parallel to the pair of guide rails.

This enables the distance between adjacent lamellas to be adapted in the form filter.

In particular the lamellas can also be arranged rotatably in the pair of guide rails. This makes a combination of rotation and translation of the lamellas in the form filter possible and enables a further increased number of adaptation options of the spatial of the x-ray beam to be achieved.

In one variant embodiment of the apparatus, at least one connection element is arranged between the holder apparatus and each lamella of the part of the plurality of lamellas, wherein the connection element has at least one actuator, which is embodied to move the lamella connected to it in a controlled manner.

In particular each individual, movable lamella can be assigned at least one actuator, which exclusively controls the movement of these individual lamellas. This enables each lamella of the mobile part of the plurality of lamellas to be moved independently of the movement of the further lamellas and the spatial intensity distribution to be independently changed very flexibly and in all subareas of the form filter.

In particular each degree of freedom of the lamella, meaning for example rotation and translation, can be assigned at least one actuator, which can carry out the associated movement in a controlled manner in each case.

In one variant embodiment of the apparatus, each lamella of the part of the plurality of lamellas is connected by at least one connection element to at least one further lamella of the plurality of lamellas, wherein the connection element has an actuator, which is embodied to move the lamellas connected to it in a controlled manner.

In particular lamellas arranged movably and immovably can also be connected by at least one connection element.

For example all adjacent lamellas can be connected, wherein each lamella can be assigned at least one actuator per adjacent lamella, which in conjunction with the further actuators assigned to the lamella, controls the movement of the respective lamella as a function of the movement of the adjacent lamellas.

For example the plurality of lamellas can also be subdivided into subsets connected to one another that do not have any movable connection between them, wherein the actuators integrated into the connection elements coordinate the movement of the lamellas of the subareas in each case.

In particular, in such cases the movement of a lamella controlled by the actuator can have an effect on all other connected movable lamellas or the connected movable lamellas can only be moved jointly. Thereby it is possible for example to achieve accumulation of the movements or a common movement of connected lamellas, which can lead to an efficient alignment of the totality of lamellas in the form filter in terms of time.

In particular however there can also be connections, which have no actuators from lamellas of the plurality of lamellas to further lamellas of the plurality of lamellas or the holder apparatus.

In one variant embodiment of the apparatus the connection element that has the actuator is further connected to the holder apparatus.

For example outer lamellas, which only have an adjacent lamella on one side or which represent an outer lamella of a subarea of lamellas, can be connected via a connection element to the holder apparatus. This enables a precise activation of even the outer lamellas or of the subareas connected to them to be made possible.

For example the connection element can have an elastic material. For example all movable lamellas can be connected in this way. However only subsets of the lamellas and/or also immovable lamellas can also be connected with the elastic material.

For example the connection element that has an elastic material has at least one actuator between at least one movable lamella and one immovable lamella or the holder apparatus. By activating the actuator the length of the elastic material can be changed for example. This enables all lamellas connected to the elastic material also to be moved.

In particular an actuator can be positioned just on one side of a group of lamellas connected in this way, wherein the elastic material can be attached on the other side of the connection to the holder apparatus or to an immovable lamella. However actuators can also be positioned on both sides between the two respective outer lamellas of the group of lamellas and the holder apparatus and/or an immovable lamella, which control the change in length of the elastic material.

Thereby a very efficient alignment in terms of time of a plurality of lamellas is possible with little outlay in terms of construction.

In variant embodiments of the apparatus the actuators have electroactive polymers or piezoelectric ceramics.

The use of electroactive polymers or piezoelectric ceramics enables the movements of the lamellas to be controlled rapidly and precisely.

At least one embodiment of the invention further relates to an irradiation arrangement, comprising:
an x-ray source for generation of the x-ray beam; and
an embodiment of the inventive apparatus disclosed,
wherein the apparatus is positioned in a position relative to the x-ray source.

At least one embodiment of the invention further relates to a medical imaging apparatus, having an inventive irradiation arrangement of at least one embodiment.

The medical imaging apparatus can be chosen for example from the group of imaging modalities that consists of an x-ray device, a C-arm x-ray device, a Computed Tomography (CT) device, a combined Single Proton Emission Computed Tomography device (SPEC-CT device) combined with a Computed Tomography device and a Positron Emission Tomography device (PET-CT device) combined with a Computed Tomography device. The medical imaging apparatus can further have a combination of an imaging modality, which for example is chosen from the imaging modality group, and an irradiation modality. In this case the irradiation modality can be an irradiation unit for therapeutic irradiation.

In particular the group of parallel straight lines, which run through the plurality of lamellas in the form filter, can be arranged both transverse to and also along the axis along which the region of the patient's body to be imaged is positioned. This enables the spatial intensity distribution to be changed both transverse to this patient axis, but also along this patient axis.

At least one embodiment of the invention further relates to an inventive medical imaging apparatus, wherein the medical imaging apparatus is a computed tomography device.

At least one embodiment of the invention further relates to an apparatus for changing a spatial intensity distribution of an x-ray beam, comprising:
a form filter, which is able to be introduced into a beam path of an x-ray beam generated by an x-ray source, wherein the form filter has a holder apparatus, in which a plurality of lamellas are arranged, wherein each lamella of the plurality of lamellas has at least one straight line running through the respective lamella in parallel to the further lamellas and further has a height profile in a plane defined by the respective lamella, wherein the height profile relates to a height of the respective lamella, which extends at right angles to the straight line running through the respective lamella and changes along the straight line running through the respective lamella; and a control unit, which is embodied to control a controlled movement of the form filter relative to the x-ray source and/or a controlled movement of lamellas of at least a part of the plurality of lamellas relative to one another and thereby to change the spatial intensity distribution of the x-ray beam.

A lamella can be embodied in particular as a planar component. For example a lamella can have a form which can be approximately represented by a flat form, in particular a rectangular plane. For example under specific conditions, in particular with a relatively slight curvature, even a lamella, which is embodied as a curved flat component can be approximately represented by a rectangular flat form.

The plane defined by the lamella can in particular have the flat form, in particular the rectangular flat form, through which the form of the lamella can be approximately represented.

In particular a greatest extent of the lamella in a direction that is at right angles to the plane defined by the lamella is significantly smaller, in particular smaller by at least a factor of ten, than the greatest extent of the lamella along any given side of the rectangular flat form, through which the form of the lamella can be approximately represented.

A thickness of the lamella can in particular be understood as an extent of the lamella in a direction that is at right angles to the plane defined by the lamella.

The height of the lamella can in particular be understood as an extent of the lamella in a direction that is parallel to a short side of the rectangular flat form by which the form of the lamella can be approximately represented. The height of the lamella can in particular change in a direction that is at right angles to the short side of the rectangular flat form by which the form of the lamella can be approximately represented.

A length of the lamella can in particular be understood as an extent of the lamella in a direction that is parallel to a long side of the rectangular flat form by which the form of the lamella can be approximately represented. The length of the lamella can in particular change in a direction that is at right angles to the rectangular flat form by which the form of the lamella can be approximately represented.

The fact that a lamella has at least one straight line running through the respective lamella can be understood in particular as the lamella having a straight line section of the straight line running through the respective lamella and/or that the rectangular flat form by which the form of the lamella can be approximately represented has a straight line section that has the straight line running through the respective lamella.

One form of embodiment makes provision for the height profile in a central area of the respective lamella to have a minimum, in particular in such a way that the x-ray beam at different locations of the straight line running through the respective lamella covers distances differing in length through the lamella and/or is attenuated the least in central areas of the respective lamella.

One form of embodiment makes provision for the height profile in edge areas of the respective lamella to have a maximum in each case. In particular the height profile can be embodied such that the x-ray beam is attenuated significantly less in the central area of the respective lamella, for example less by at least the factor 3, in particular less by the factor 10, than in the edge areas of the respective lamella.

One form of embodiment makes provision for the height profile to be embodied symmetrically.

One form of embodiment makes provision for the height profile to be embodied steplessly.

One form of embodiment makes provision for the height profile to be embodied in a curved shape.

One form of embodiment makes provision for each lamella of the plurality of lamellas to have a straight long edge and/or for the straight long edge to be parallel to the straight line running through the respective lamella and/or to lie on the straight line running through the respective lamella.

One form of embodiment makes provision for each lamella of the plurality of lamellas to have a curved long edge and/or for the curved long edge to lie in the plane defined by the respective lamella.

In particular each lamella of the plurality of lamellas can have two curved long edges, in particular in such a way that each lamella in a central area of the lamella has a narrow section. In particular each lamella of the plurality of lamellas can be embodied in the shape of a bow-tie. In particular there can be provision for the straight line running through the respective lamella to run through the narrow section in the central area of the respective lamella.

One form of embodiment provides for an apparatus as in one of the disclosed embodiments, further comprising a positioning unit, which interacts with the control unit and which is embodied to move the form filter relative to the x-ray source in a controlled manner and/or to move the lamellas of the at least one part of the plurality of lamellas relative to one another in a controlled manner.

At least one embodiment of the invention further relates to a computed tomography device, comprising:

an x-ray source and an x-ray detector which interacts with the x-ray source, wherein the x-ray source and the x-ray detector are arranged about a system axis of the computed tomography device, which is located rotatably between the x-ray source and the x-ray detector; and an apparatus for changing a spatial intensity distribution of an x-ray beam of an embodiment of one of the disclosed aspects, wherein the form filter is arranged between the x-ray source and the system axis.

One form of embodiment makes provision for the lamellas of the plurality of lamellas to be aligned on the focus line. A lamella is in particular aligned on the focus line when the focus line lies in the plane defined by the lamella. The focus line can in particular be understood as a line on which the lamellas of the plurality of lamellas are focused. In particular the focus line can be essentially parallel to the system axis. In particular the focus line can lie in a plane that is at right angles to the system axis.

Further pluralities of lamellas can be provided that differ relative to one another in relation to the focus lines on which the lamellas are aligned, and/or in relation to the height profiles of the lamellas. In particular there can be provision for the form filter, in addition to the plurality of lamellas that are aligned on a focus line, to have a further plurality of further lamellas that are aligned on a further focus line. In particular there can be provision for each further lamella of the further plurality of further lamellas to have at least one straight line running through the respective further lamella, which is parallel to the further lamellas of the further plurality of lamellas and is not parallel to the lamellas of the plurality of lamellas. The form filter, in addition to the lamellas of the plurality of lamellas can further have one or more further lamellas, of which the characteristics, in particular geometric characteristics, deviate from corresponding characteristics of the lamellas of the plurality of lamellas.

The greater the height of the lamella is, the greater is the effect of a rotation of the lamella on the attenuation of the x-ray beam. In particular with a distance between adjacent lamellas that cannot be changed, a characteristic value, which essentially corresponds to the grid ratio in anti-scatter grids, also changes with the height of the lamella along the straight line running through the respective lamella. The dose profile can thus be influenced by the height profile of the lamellas.

The lamellas can be manufactured in particular from a material that strongly absorbs x-rays, for example from lead and/or tungsten.

Within the framework of embodiments of the invention, features that are described in relation to different forms of embodiment of the invention and/or different claim categories (method, use, apparatus, system, arrangement etc.), can be combined into further forms of embodiment of the invention. For example a claim that relates to an apparatus can also be further developed with features that are described or claimed in conjunction with a method and vice versa. Functional features of a method can in such cases be carried out by correspondingly embodied physical components. As well as the forms of embodiment of the invention expressly described in this application, numerous further forms of embodiment of the invention are conceivable, at which the person skilled in the art can arrive without departing from the field of the invention that is specified by the claims.

The use of the indefinite article "a" or "an" does not exclude the feature involved also being able to be present more than once. The use of the expression "have" does not exclude the terms linked via the term "have" being able to be identical. For example the computed tomography device has the computed tomography device. The use of the expression "unit" does not exclude the subject matter to which the expression "unit" relates being able to have a number of components, which can also be physically separated from one another.

FIG. 1 shows a schematic view of a medical imaging apparatus with an inventive irradiation arrangement of an embodiment.

Without restricting the general ideas of the invention, a computed tomography device 1 (CT device) of an embodiment is shown as an example of the medical imaging apparatus.

The CT device 1 has a gantry with a rotating ring 3 and a stationary support frame 5. The rotating ring 3 is supported rotatably in relation to the system axis 7. When the CT device 1 is operating the body of a patient 9 is positioned in the space surrounded by the rotating ring 3 in such a way that the system axis 7 runs through the patient's body 9. Inter alia an x-ray source 11 is arranged on the rotating ring 3, which generates an x-ray beam 15 emanating from a generation point 13. The beam path 17 of the x-ray beam 15 runs in this case from the generation point 13 in a fan shape in the direction of the patient's body 9. The CT device 1 now has an apparatus 19 for changing a spatial intensity distribution of the x-rays 15. The apparatus 19 here comprises a form filter 21 with a plurality of lamellas 23, which is positioned in the immediate vicinity of the generation point 13 in the beam path 17, and also a control unit 25. The control unit 25 in this case is embodied by suitable device(s) to control the movement of at least one part of the plurality of lamellas 23 in a controlled manner and thereby to change the spatial intensity distribution of the x-ray beam 15 in such a way that the radiation intensity striking the patient's body 9 is as optimal as possible at any point in time of the operation of the CT device 1 both in respect of the image resolution and also in respect of medical criteria.

Figure 2:
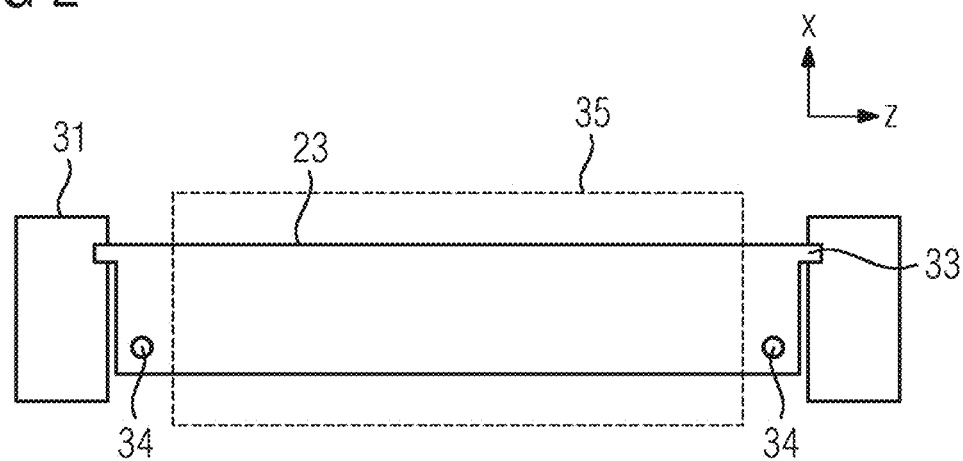
FIG. 2 shows a schematic longitudinal section through a form filter of one form of an embodiment.

FIG. 2 shows a schematic of a longitudinal section through a form filter 21 for changing an intensity distribution of an x-ray beam 15 of one form of embodiment. The coordinate axis x of the coordinate system shown in FIG. 2 and in the following FIGS. 3 to 9 can in this case as a rule run essentially in parallel to a central axis of the x-ray beam 15. The coordinate axis z of the coordinate system shown can as a rule be aligned both in parallel and also at right angles to the system axis 7, about which the rotating ring 3 rotates. Accordingly this also applies to the coordinate axis y lying at right angles to x and z.

The form filter 21 comprises a holder apparatus 31 on which the lamella 23 is arranged. The section shows an example of a lamella 23 of the plurality of lamellas in the form filter 21, which is arranged on two opposite sides of the holder apparatus 31. For example the lamella 23 is arranged via guide pins 33 movably on the holder apparatus 31.

The lamella 23 shown by way of example moreover has engagement points 34 for controlled movement of the lamella 23 relative to the further lamellas. These device(s) can for example be embodied as they are below in relation to FIGS. 3 to 9 as connection device(s), which comprise actuators. By way of example the engagement points 34 are arranged on the lower long edge of the lamella 23 opposite to the guide pins 33. The engagement points 34 can also be positioned in other forms of embodiment in other ways on the lamella 23. The lamellas 23 can also have just one or more than two engagement points 34.

Advantageously the engagement points 34 can be positioned outside the radiation field 35 illuminated by the beam path of the x-ray beam, in order not to additionally influence the x-ray flux and to minimize scattered radiation.

Figure 3:
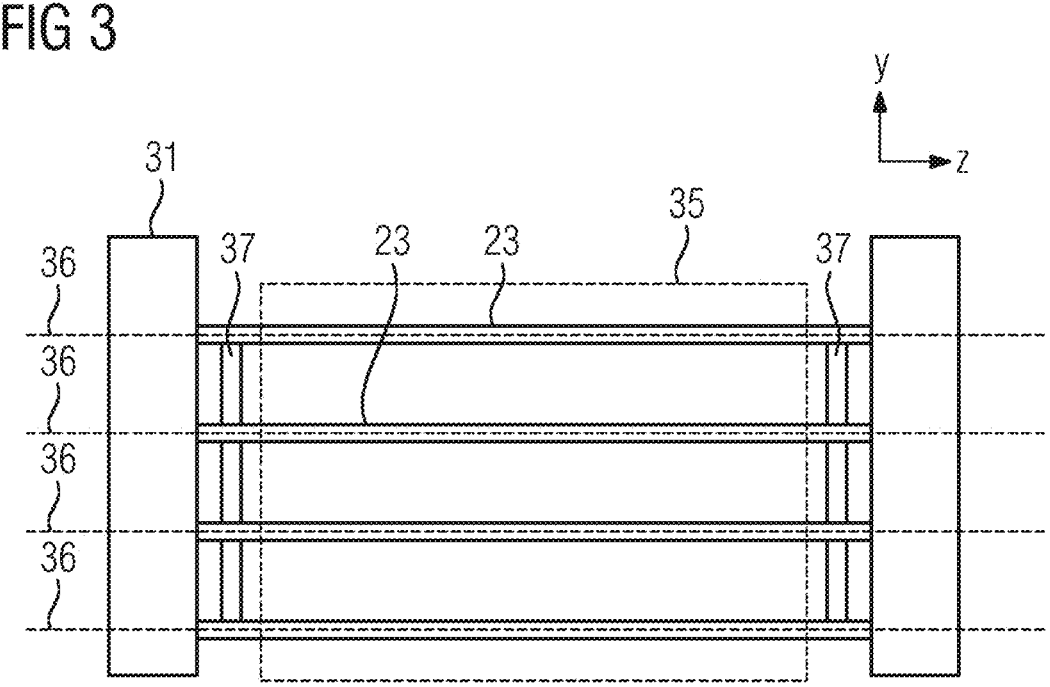
FIG. 3 shows a schematic overhead view of a form filter with a plurality of lamellas of one form of an embodiment.

FIG. 3 shows a schematic of an overhead view of a form filter 21 with a plurality of lamellas 23, which are arranged on the holder apparatus 31. The number of lamellas shown is merely by way of example and for illustration, the form filter 21 can also have more or fewer and both movably and also immovably arranged lamellas 23.

The plurality of lamellas 23 is arranged on the holder apparatus 31 in such a way that each lamella 23 has at least one straight line 36 running through the respective lamella, which runs in parallel to the further lamellas. In the exemplary embodiment shown only the end-face edges of flat-design lamellas 23 are to be seen, wherein the straight lines 36 of the parallel group of straight edges run in parallel to the end-face edge of the lamellas 23. The group of parallel straight lines 36 in this case as a rule runs either in parallel or also at right angles to the axis 7 about which the rotating ring 3 rotates. The distances between adjacent lamellas are chosen as the same by way of example. In alternate forms of embodiment of the form filter 21 the distances can also be different or also adapted before, during or after operation of the form filter and thus also chosen differently in different operating states of the form filter.

In the form of embodiment shown all adjacent lamellas are connected by connection elements 37. In other forms of embodiment however just subsets of the lamellas 23 can be connected. The connection elements 37 can have actuators, which are embodied to move the lamellas 23 relative to one another in a controlled manner.

The activation of an actuator can lead to a change in length of a corresponding connection element 37, which brings about a movement of the lamellas relative to one another.

In particular the connection elements 37 can be positioned outside the radiation field 35 illuminated by the beam path 17 of the x-ray beam 15, in order not to additionally influence the flux of x-rays and to minimize scattered radiation.

Figure 4:
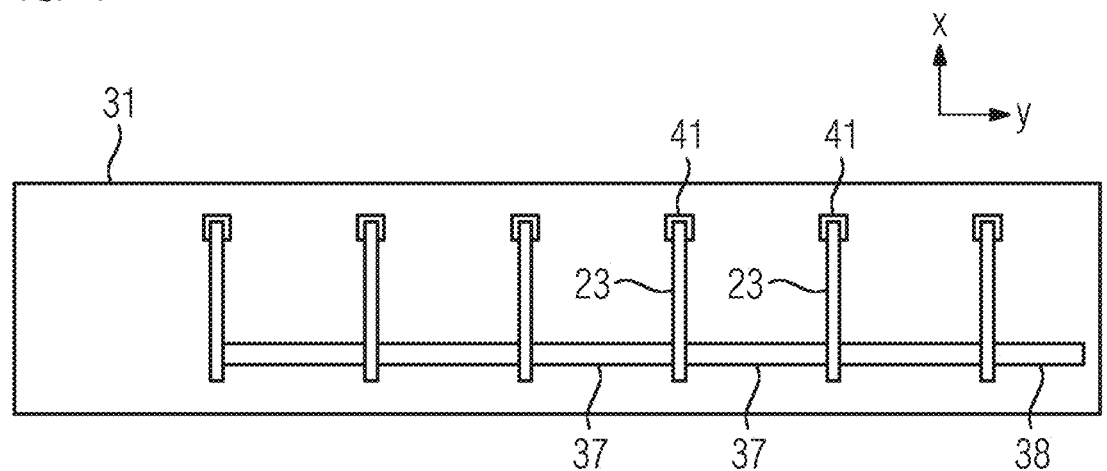
FIG. 4 shows a schematic cross-section through a form filter with a plurality of lamellas in a further form of embodiment.

Shown in FIG. 4 is a schematic view of a cross-section of a form filter 21 of an embodiment. In the exemplary embodiment the holder apparatus 31 has mounting points 41, via which a plurality of lamellas 23 are arranged rotatably on the holder apparatus 31. Each mounting point 41 is assigned a second mounting point 41 on the opposite side of the holder apparatus 31 not shown here. The mounting points 41 each form pairs of mounting points between which the lamellas 23 are arranged. The distance between adjacent lamellas 23 is determined by the arrangement of the mounting points 41 in the holder apparatus 31. In this exemplary embodiment the distances between all adjacent lamellas are chosen as the same, but they can also differ however.

In the form of embodiment shown each lamella 23 of the plurality of lamellas 23 is connected via a connection element 37 to the respective adjacent lamellas. Moreover the exemplary embodiment has a lamella connected via a connection element 38 to the holder apparatus 31, which can contribute to a more stable and more precise alignment of the connected lamellas.

Figure 5:
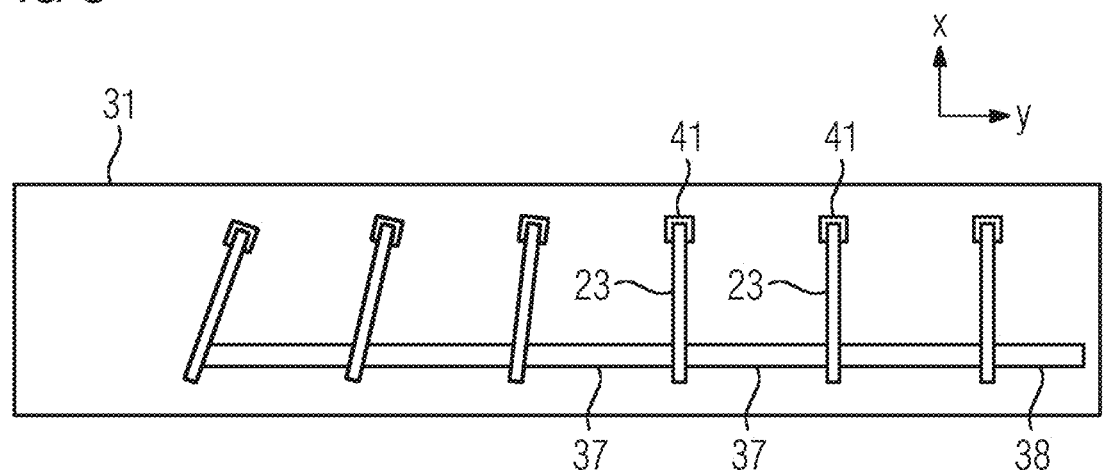
FIG. 5 shows the form filter shown in FIG. 4 in another operating state of the form filter.

FIG. 5 shows a schematic of the form filter 21 shown in FIG. 4 in another operating state of the form filter. By changing the length of at least one subset of the connection elements 37, lamellas 23 of the plurality of lamellas 23 have been moved relative to the further lamellas. The change in length can be brought about for example by the activation of actuators in the connection elements 37.

In the form of embodiment shown the change in length of the connection elements 37 causes a rotation of the lamellas 23 about an axis of rotation parallel to the respective upper long edge of the lamellas 23 through the respective mounting points 41. The axis of rotation of each lamella 23 in this case corresponds in each case to the straight line 36 running through the lamella in parallel to the further lamellas. The group of axes of rotation of the lamellas 23 thus corresponds to the group of parallel straight lines 36 in FIG. 3. In other forms of embodiment of the form filter the axis of rotation can also run to the side of the straight line 36 running through the lamella in parallel to the further lamellas.

This enables the plurality of the lamellas 23 to be aligned relative to the beam path 17 of the x-ray beam 15 through the movement of at least one part of the plurality of lamellas 23 and the intensity distribution of the x-ray beam 15 to be changed. In the form of embodiment shown the lamellas 23 can be positioned with a fixed distance arrangement of the plurality of lamellas 23 running both to one and also to different focus points/focus lines. The rotational movement makes it possible to control the alignment of the plurality of lamellas 23 precisely and predictably. For example in this way both convex and concave intensity profiles but also other types of intensity profiles can be created.

In particular in this case the controlled movement of one lamella 23 can have an effect on all other connected movable lamellas. This makes it possible for example to achieve accumulation of the movements or a joint movement of connected lamellas 23, which can lead to an efficient alignment of the plurality of lamellas in the form filter in terms of time.

The connection of a lamella 23 via a connection element 38 to the holder apparatus 31 can in this case be part of a stable alignment of the plurality of lamellas in the form filter 21. Forms of embodiment are also possible however that do not have any connection elements 38 between lamellas 23 and the holder apparatus 31. Also not all connected lamellas have to be arranged movably in the form filter 21. Also just subsets of the lamellas can be connected to one another.

Figure 6:
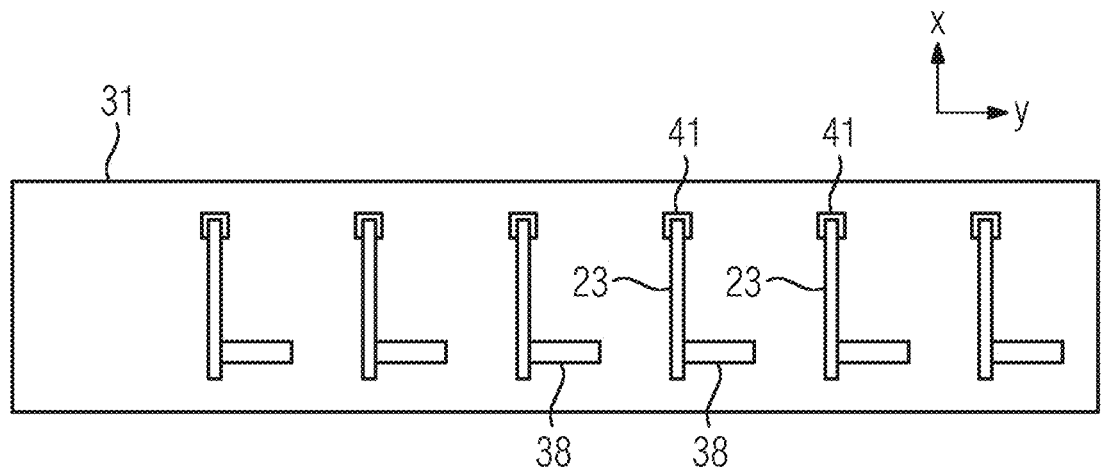
FIG. 6 shows a schematic cross-section through a form filter with a plurality of lamellas in a further form of embodiment.

FIG. 6 shows a schematic cross-section of a form filter 21 of an embodiment, wherein the lamellas 23 are arranged rotatably in mounting points 41 in the holder apparatus 31. Each individual lamella 23 in this case is assigned at least one connection element 38 between lamella and holder apparatus, which comprises at least one actuator. In this form of embodiment the activation of an actuator causes a rotation of a lamella 23 about an axis of rotation parallel to the upper long edge and through the mounting point 41. Each lamella 23 is moved independently of the further lamellas in the form filter 21. This enables the spatial intensity distribution to be changed independently very flexibly and in all subareas of the form filter.

Figure 7:
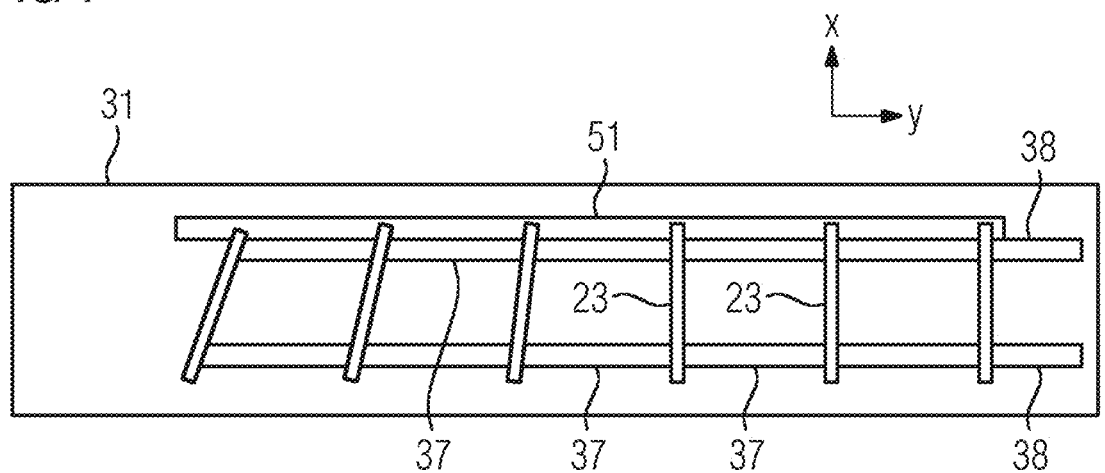
FIG. 7 shows a schematic cross-section through a form filter with a plurality of lamellas in a further form of embodiment.

FIG. 7 shows a schematic cross-sectional view of a form filter 21 of an embodiment that, instead of the mounting points 41, has a guide rail 51 in the holder apparatus 31. The opposite part of the holder apparatus 31 not shown comprises a corresponding guide rail 51 running parallel to the guide rail 51 shown. The lamellas 23 are arranged movably along the pairs of guide rails 51. In this example the lamellas 23 are also arranged rotatably in the guide rail 51. This enables both the distance between adjacent lamellas 23 in the form filter 21 to be adapted by a translation along the guide rail 51 and also the lamellas 23 to be positioned relative to one another by a rotation about an axis of rotation parallel to the upper long edge of the lamellas 23 running to one or more different focus points or focus lines.

The lamellas 23 are connected via connection elements 37, which can comprise actuators, which can carry out the movement of the lamellas 23 relative to one another, both rotation and also translation, in a controlled manner.

For example the lamellas 23 can be fixed in their position after they have been moved by connection elements 38 attached between lamellas and the holder apparatus 31, in order to be able to suppress an uncontrolled movement of the totality or of parts of the lamellas. There are also other forms of embodiment as well without connection device(s) 38. Other suitable device(s) are also possible that allow a stable positioning of the lamellas in the guide rail. For example through a connection to a non-movable lamella or through an option of latching the lamellas in the guide rail 51 or to the holder apparatus 31.

Figure 8:
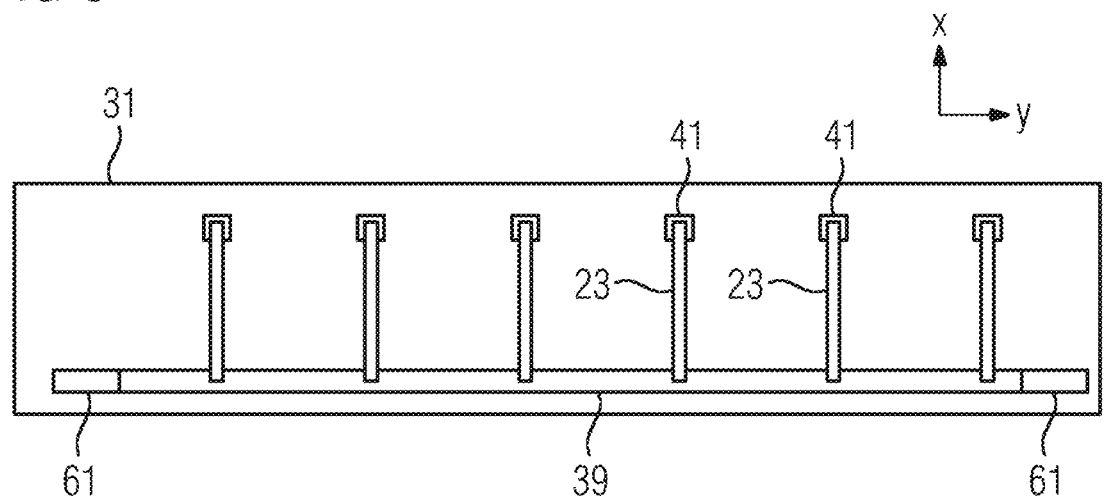
FIG. 8 shows a schematic cross-section through a form filter with a plurality of lamellas of one form of an embodiment.

Shown in FIG. 8 is a schematic cross-section of a form filter 21 of an embodiment, wherein the lamellas 23 are arranged rotatably via mounting points 41 on the holder apparatus 31 and are connected via a connection element 39, which has an elastic material. The connection element 39, which is moreover also connected to the holder apparatus 31, also comprise two actuators 61, which are arranged here by way of example on the outer ends of the connection element 39 and which are embodied to change the length of the connection element 39.

Alternative forms of embodiment can also comprise just one actuator 61 at one end. Just subsets of the lamellas 23 and also non-movable lamellas can also be connected with the connection element 39.

Figure 9:
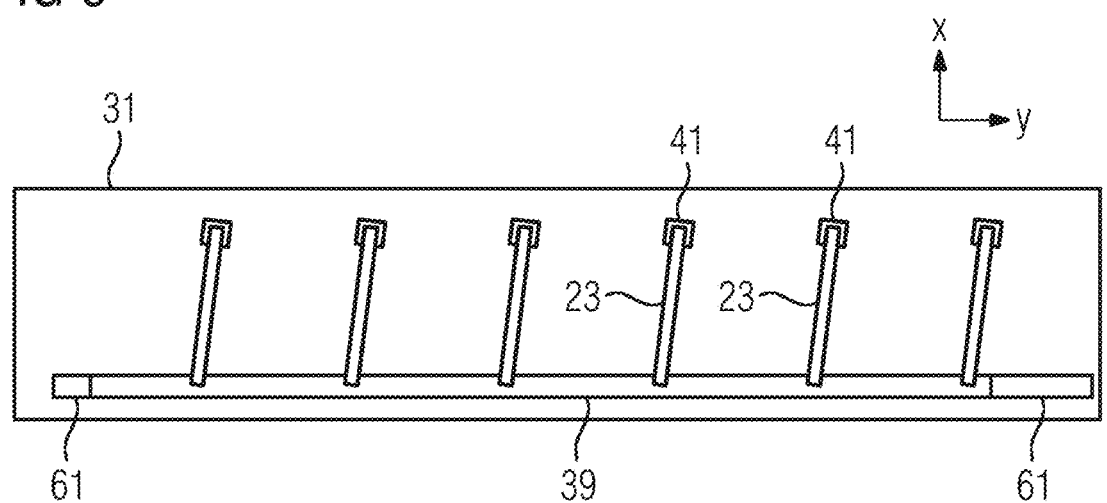
FIG. 9 shows the form filter shown in FIG. 8 in another operating state of the form filter.

FIG. 9 shows a schematic cross-section of the form filter 21 shown in FIG. 8 in another operating state.

By contrast with the view in FIG. 8, the lamellas 23 are moved relative to one another through a change of the connection element 39 brought about by an activation of the actuator 61. The change of the connection element 39 leads to a rotation of the lamellas 23 about an axis of rotation in parallel to the upper long edge of the lamellas and through the mounting points 41. A very efficient alignment of a plurality of lamellas is thereby possible in terms of time with little outlay in terms of construction. Changes of the connection element 39 can for example be changes in length of the part area of the connection element 39 that comprises the elastic material or movements of this part area relative to its starting position or also the combination of both options.

Figure 10:
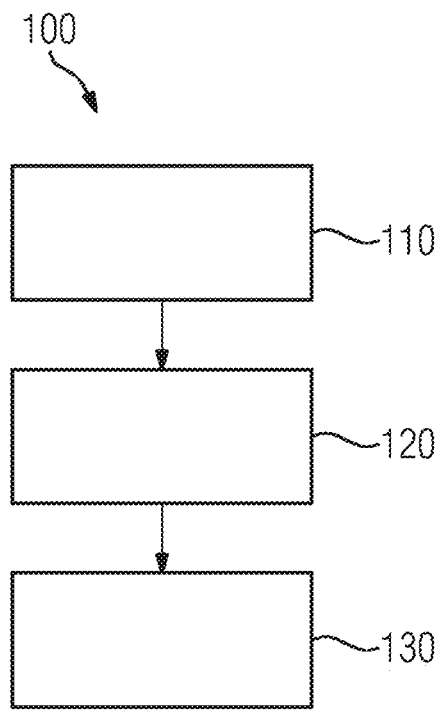
FIG. 10 shows a schematic block diagram for a method for changing a spatial intensity distribution of an x-ray beam.

FIG. 10 shows a schematic in a block diagram of a method 100 for changing a spatial intensity distribution of an x-ray beam 15.

In step 110 an x-ray beam 15 is generated by an x-ray source 11. In step 120 the beam path 17 of the x-ray beam 15 is guided through a form filter 21, which comprises a plurality of lamellas 23. In step 130 the plurality of lamellas 23 is aligned relative to the beam path 17, in that at least a part of the plurality of lamellas 23 are moved relative to one another in a controlled manner, whereby the spatial intensity distribution of the x-ray beam 15 is changed.

Figure 11:
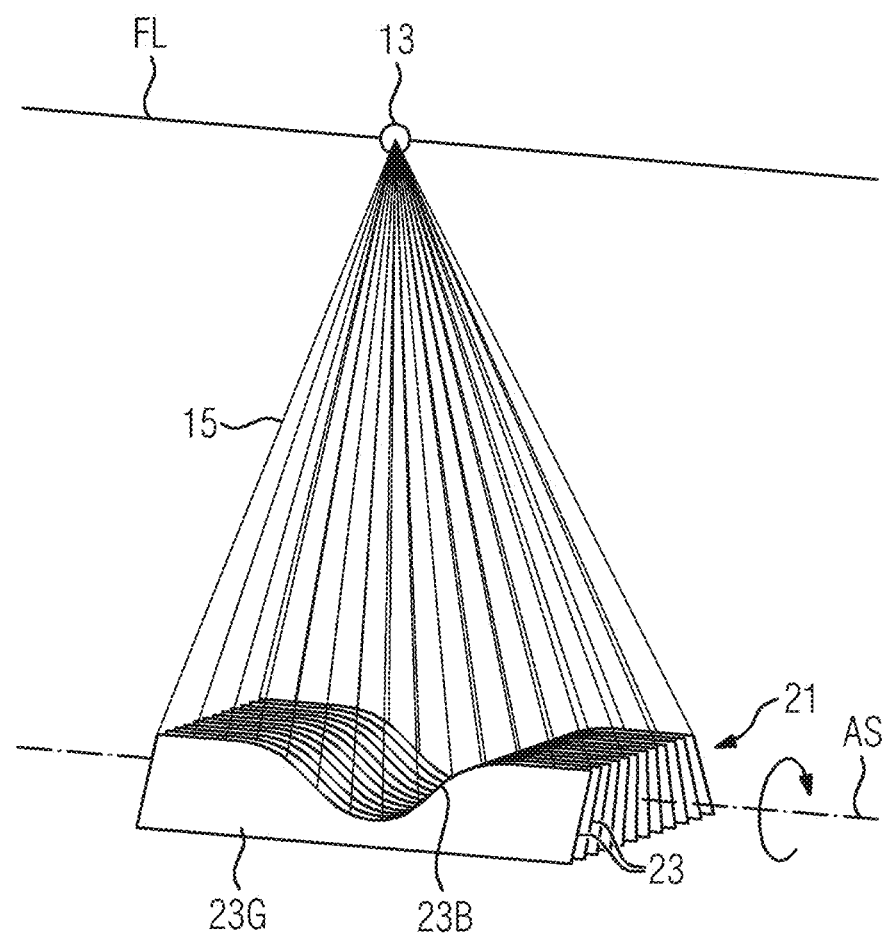
FIG. 11 shows a schematic view of a form filter with a plurality of lamellas in a further form of embodiment.

FIG. 11 shows a schematic of a form filter 21 of an embodiment with a plurality of lamellas 23, which is able to be introduced into a beam path 17 of the x-ray beam 15 generated by an x-ray source 11. Each lamella 23 of the plurality of lamellas 23 in this form of embodiment has a curved long edge 23B, wherein the curved long edge 23B lies in the plane defined by the respective lamella 23.

Figure 12:
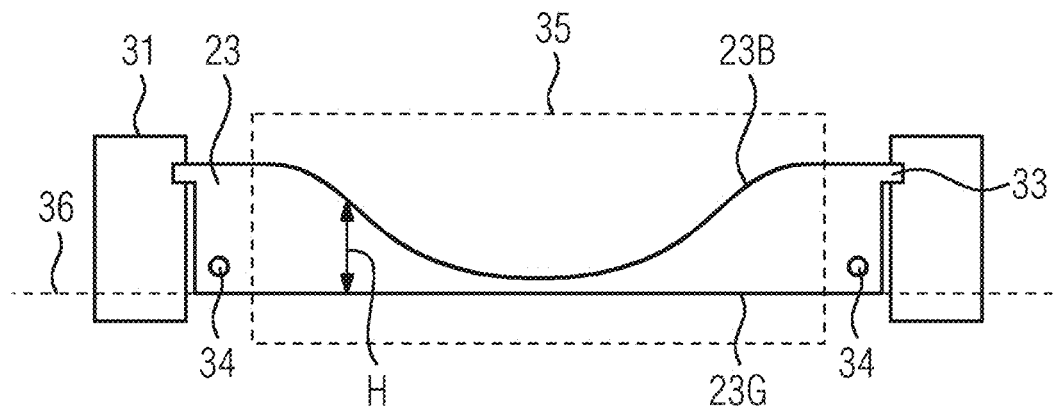
FIG. 12 shows a schematic view of a form filter with a plurality of lamellas in a further form of embodiment.

FIG. 12 shows a schematic cross-sectional view of a form filter 21 of an embodiment with a plurality of lamellas 23, wherein the form filter 21 comprises a holder apparatus 31 in which a plurality of lamellas 23 is arranged, wherein each lamella 23 of the plurality of lamellas 23 has a straight line 36 running through the respective lamella 23 in parallel to the further lamellas 23 and further has a height profile in a plane defined by the respective lamella 23, wherein the height profile relates to a height H of the respective lamella 23, which extends at right angles to the straight line 36 running through the respective lamella 23 and changes along the straight line 36 running through the respective lamella 23.

The height profile has a minimum in a central area of the respective lamella 23 and a maximum in the edge areas of the respective lamella 23 in each case. The height profile is embodied symmetrically, steplessly and in a curved shape. Each lamella 23 of the plurality of lamellas 23 has a straight long edge 23G, wherein the straight long edge 23G is parallel to the straight line 36 running through the respective lamella 23 and lies on the straight line 36 running through the respective lamella 23.

Each lamella 23 of the plurality of lamellas 23 is arranged movably on the holder apparatus 31 via guide pins 33. Each lamella 23 of the plurality of lamellas 23 has engagement points 34 for controlled movement of the respective lamella 23 relative to the further lamellas. These device(s) can for example be embodied as connection device(s) that comprise actuators. Advantageously the engagement points 34 can be positioned outside the radiation field 35 illuminated by the beam path 17 of the x-ray beam 15, in order not to additionally influence the flux of x-rays and to minimize scattered radiation.

Figure 13:
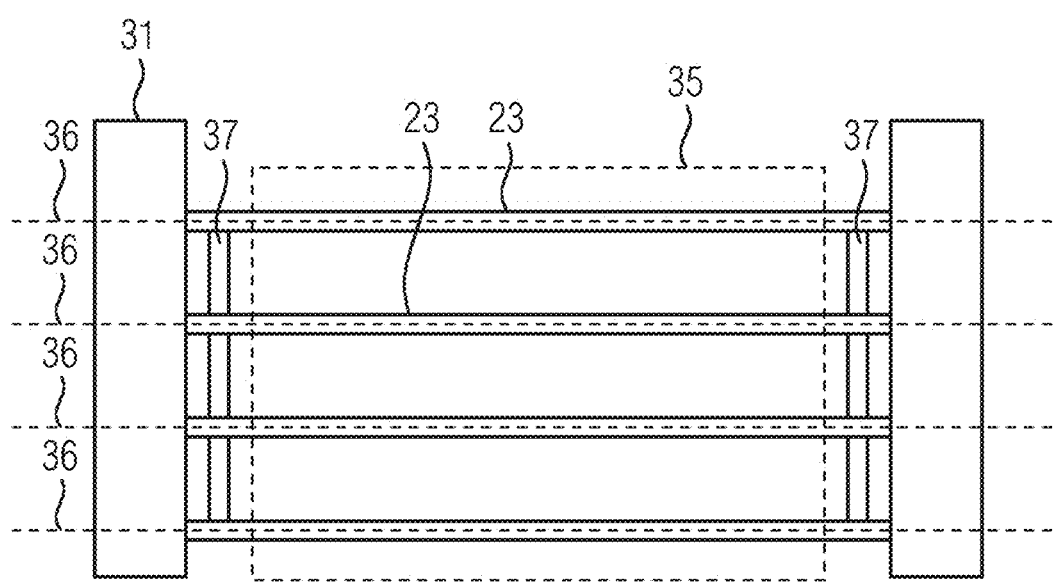
FIG. 13 shows a schematic overhead view of a form filter with a plurality of lamellas.

FIG. 13 shows an overhead view of a form filter 21 with a plurality of lamellas 23. Adjacent lamellas 23 are each connected by connection elements 37. The connection elements 37 can have actuators that are embodied to move the lamellas 23 relative to one another in a controlled manner.

Figure 14:
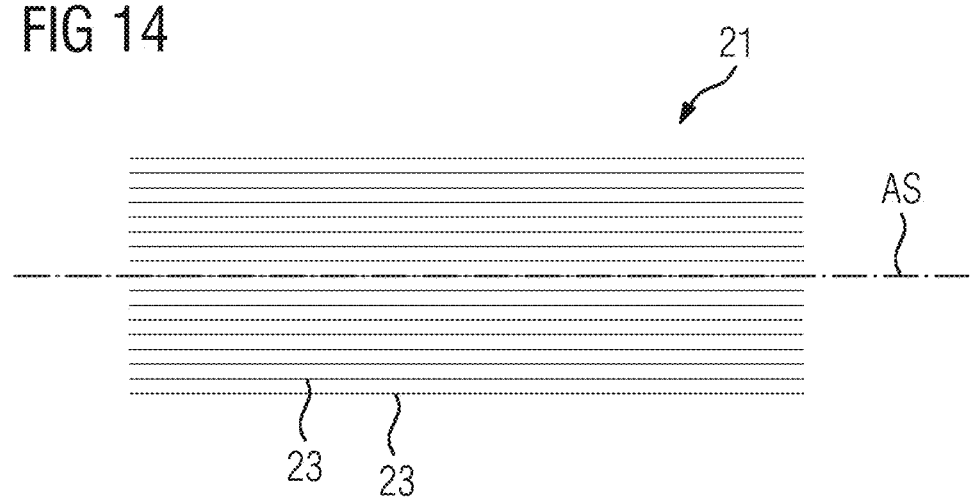
FIG. 14 shows a schematic overhead view of a form filter of which the lamellas are focused on a generation point of the x-rays.

FIG. 14 shows a schematic overhead view of a form filter 21, of which the lamellas 23 are focused on the generation point 13 of the x-ray beam 15, viewed from the generation point 13.

Figure 15:
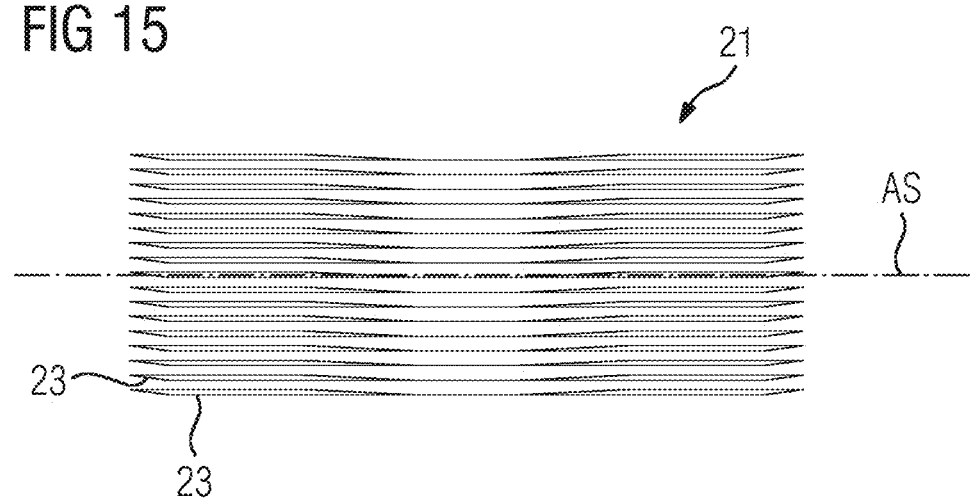
FIG. 15 shows a schematic overhead view of a form filter of which the lamellas are defocused in relation to the generation point of the x-rays.

FIG. 15 shows a schematic overhead view of a form filter 21, of which the lamellas 23 are defocused with regard to the generation point 13 of the x-ray beam 15, viewed from the generation point 13.

Figure 16:
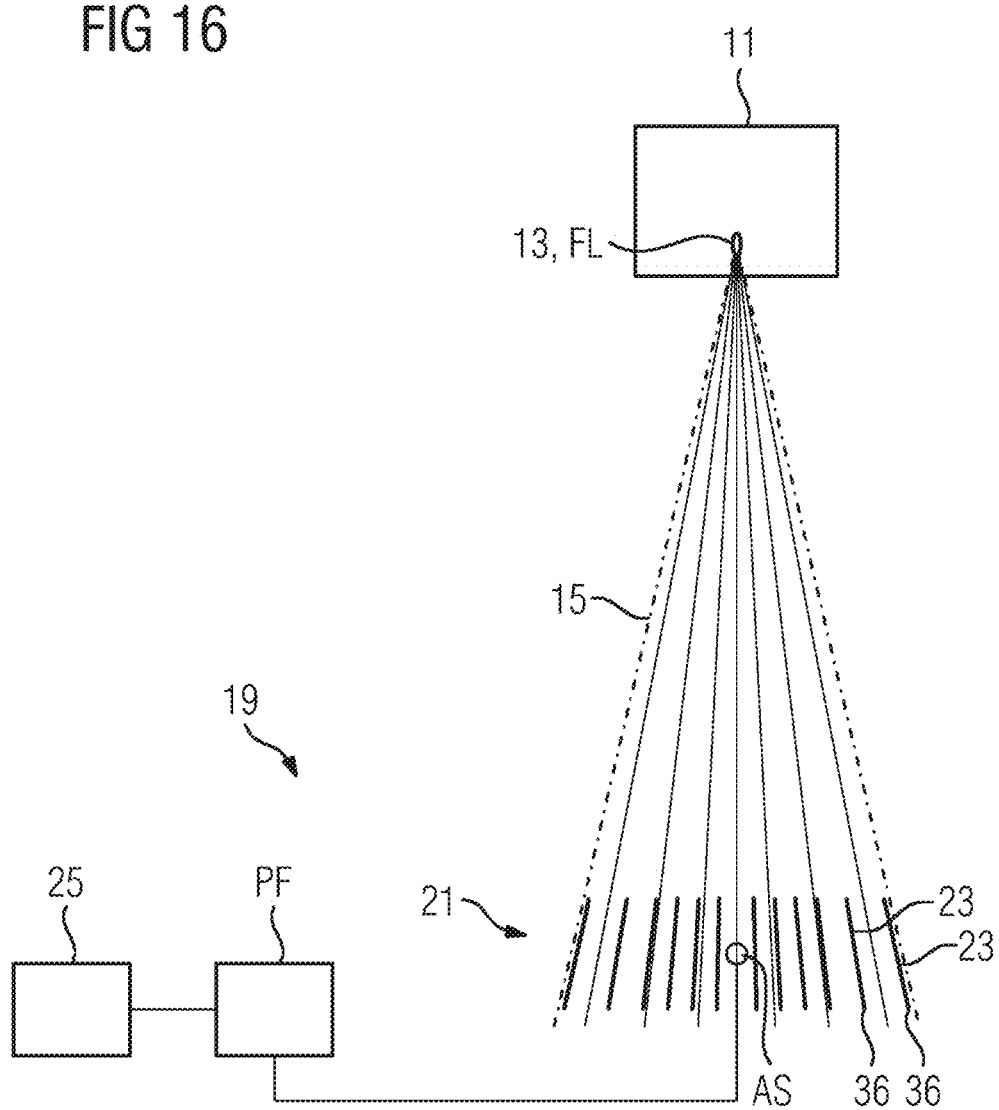
FIG. 16 shows a schematic view of an apparatus of an embodiment with a form filter, a positioning unit and a control unit.
Figure 16:
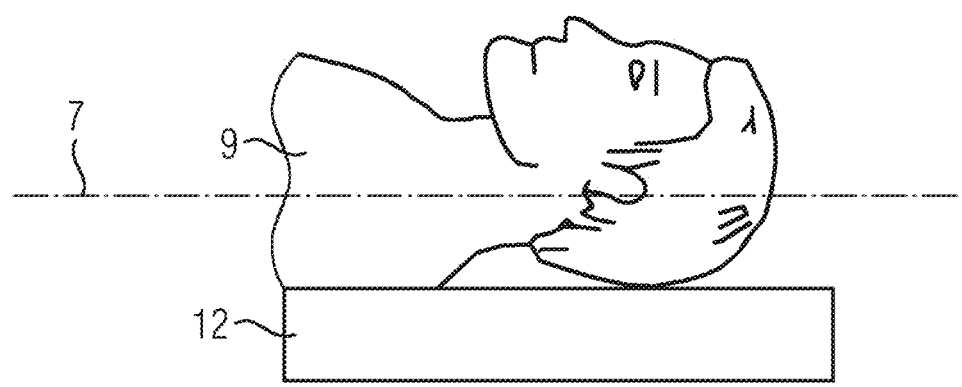

FIG. 16 shows a schematic view of an apparatus 19 with a form filter 21, a positioning unit PF and a control unit 25.

The control unit 25 is embodied to control a controlled movement of the form filter 21 relative to the x-ray source 11 and/or a controlled movement of lamellas 23 of at least a part of the plurality of lamellas 23 relative to one another and thereby to change the spatial intensity distribution of the x-ray beam 15. The positioning unit PF interacts with the control unit 25 and is embodied to move the form filter 21 relative to the x-ray source 11 in a controlled manner and/or to move the lamellas 23 of the at least one part of the plurality of lamellas 23 relative to one another in a controlled manner.

The lamellas 23 of the plurality of lamellas 23 are aligned to a focus line FL. The focus line FL lies in a plane that is at right angles to the axis of rotation 7. The lamellas 23 thus extend essentially along a width of a fan of radiation of the x-ray beam 15. The lamellas 23 are essentially at right angles to a plane in which the system axis 7 and the generation point 13 are located.

By swiveling the form filter 21 about the swivel axis AS the spatial intensity distribution of the x-ray beam 15 can be changed. Thus an optimal dose profile can be generated. The swivel axis AS is parallel to the focus line FL and parallel to the lamellas 23. For defocusing it is in particular sufficient to rotate the form filter 21 relative to the x-ray source 11 by a few degrees. This movement and thus the change in the intensity distribution can thus be made relatively rapidly. As an alternative or in addition to the swivel movement about the swivel axis AS a translation movement of the form filter 21 relative to the x-ray source 11, in particular in parallel to the system axis 7 and/or in the direction of a central ray of the x-ray beam 15, can be provided.

The structure of the form filter 21 shown in FIG. 16 is low-frequency in the direction of a width of the fan of radiation of the x-ray beam 15. This enables artifacts in the image in the form of fine rings to be avoided. The transmission profile of the intensity distribution of the x-ray beam 15 depends in particular on the height profile of the lamellas 23. By choosing a correspondingly suitable height profile of the lamellas 23 different transmission profiles are able to be realized, in particular also transmission profiles that do not have the shape of a triangle.

A diaphragm, which restricts the beam path 17 of the x-ray beam 15 in the direction of the axis of rotation 7, can be arranged between the x-ray source 11 and the form filter 21 or between the form filter 21 and the system axis 7 for example. The form filter 21 composed of the lamellas 23 radiates comparatively less secondary radiation than a corresponding filter embodied of solid material.

FIG. 17 shows a schematic view of a computed tomography device 1 (CT device) of an embodiment, comprising the following components:

An x-ray source 11 and an x-ray detector 28, which interacts with the x-ray source 11, wherein the x-ray source 11 and the x-ray detector 28 are arranged rotatably about a system axis 7, which is located between the x-ray source 11 and the x-ray detector 28, and An apparatus 19 for changing a spatial intensity distribution of an x-ray beam 15, wherein the form filter is arranged between the x-ray source 11 and the system axis 7.

The computed tomography device 1 has a gantry 20 with a rotating ring 3 and a stationary support frame 5. The rotating ring 3 is supported rotatably with regard to the system axis 7 relative to the stationary support frame 5. Optionally the rotating ring 3 is additionally supported tiltably relative to the stationary support frame 5. In operation of the CT device 1 the patient's body 9 is positioned in such a way in the space surrounded by the rotating ring 3 that the system axis 7 runs through the patient's body 9. Arranged on the rotating ring 3 inter alia is an x-ray source 11, which generates an x-ray beam 15 starting from a generation point 13. The beam path 17 of the x-ray beam 15 in this case runs outwards from the generation point 13 in a fan shape in the direction of the patient's body 9. The CT device 1 now has an apparatus 19 for changing a spatial intensity distribution of the x-rays 15. The apparatus 19 here comprises a form filter 21 with a plurality of lamellas 23, which is positioned in the immediate vicinity of the generation point 13 in the beam path 17, as well as a control unit 25. The control unit 25 is embodied in this case to control in a suitable way the movement of at least a part of the plurality of lamellas 23 in a controlled manner and thereby to change the spatial intensity distribution of the x-ray beam 15 in such a way that the radiation intensity striking the patient's body 9 at any point in time during the operation of the CT device 1 both in respect of the image quality, in particular in respect of the signal-to-noise ratio, and also in respect of medical criteria, in particular in respect of the dose, is as optimal as possible.

The CT device 1 further has the tunnel-shaped opening 8. The patient's body 9 is able to be introduced into the tunnel-shaped opening 8. Located in the tunnel-shaped opening 8 is the acquisition area 4. An area of the patient's body 9 to be imaged is able to be positioned in the acquisition area 4 in such a way that the x-ray beam 15 can get from the x-ray source 11 to the region to be imaged and after an interaction with the region to be imaged, can reach the x-ray detector 28.

The CT device 1 further has a patient support apparatus 10 with the support pedestal 14 and the support table 12 for supporting the patient's body 9. The support table 12 is arranged movably relative to the support pedestal 14 on the support pedestal in such a way that the support table 12 is able to be introduced in a longitudinal direction of the support table 12, in particular essentially along the system axis 7, into the acquisition area 4.

The CT device 1 further has the positioning unit PF. The positioning unit PF has a form filter positioning module PFL, which is embodied for positioning the form filter 21 relative to the x-ray source 11. The positioning unit PF further has a lamella positioning module PFM, which is embodied for positioning the lamellas 23 of the form filter 21 relative to one another. The positioning unit PF is thus embodied for positioning the form filter 21 relative to the x-ray source 11 and for positioning the lamellas 23 of the form filter 21 relative to one another. The form filter 21 is connected via the form filter positioning module PFL to the rotor 24. The form filter positioning module PFL can have a gimbal for example.

The CT device 1 further has the deflection apparatus AV, which is embodied to set a deflection of an electron beam in the x-ray source 11 in such a way that a predetermined location of the generation points 13 relative to the focus line FL can be set. In particular the x-ray source 11 can involve a spring focus x-ray source. The detector 28 can in particular be an energy-resolving x-ray detector.

The CT device 1 further has the control apparatus C0, which is embodied to control the CT device 1. The control apparatus C0 has the control unit 25, the computer-readable medium C2 and the processor system C6. The control apparatus C0 in particular the control unit 25, is formed by a data processing unit, which has a computer. The control apparatus C0 has the image reconstruction facility C4. By way of the image reconstruction facility C4 a medical image dataset can be reconstructed based on the acquisition data.

The CT device 1 further has an input apparatus C8 and an output apparatus C9, which are each connected to the control apparatus C0. The input apparatus C8 is embodied for input of control information, e.g. image reconstruction parameters, examination parameters or the like. The output apparatus C9 is in particular embodied for output of control information, images and/or acoustic signals.

Although the invention has been illustrated and described in greater detail by exemplary embodiments, the invention is not restricted by these exemplary embodiments. Other variations can be derived herefrom by the person skilled in the art, without departing from the scope of protection of the invention.

The invention claimed is:

1. A method for changing a spatial intensity distribution of an x-ray beam, comprising:
    generating an x-ray beam via an x-ray source;
    guiding a beam path of the x-ray beam through a form filter with a plurality of lamellas, the form filter including a holder apparatus, wherein the plurality of lamellas are arranged in the holder apparatus such that each respective lamella, of the plurality of lamellas, has at least one straight line running through the respective lamella in parallel to other of the plurality of lamellas; and
    aligning the plurality of lamellas relative to the beam path by controlled movement of at least one part of the plurality of lamellas relative to other of the plurality of lamellas, to change the spatial intensity distribution of the x-ray beam.

2. The method of claim 1, wherein the plurality of lamellas are aligned by a rotation of each respective lamella of the part of the plurality of lamellas about an axis of rotation.

3. The method of claim 1, wherein the plurality of lamellas are aligned by a translation of each respective lamella of the part of the plurality of lamellas at right angles to the straight line running through the respective lamella in parallel to the other of the plurality of lamellas.

4. The method of claim 1, wherein the aligning of the plurality of lamellas is set by a movement of each respective lamella of the part of the plurality of lamellas, independently of the movement of the other of the plurality of lamellas.

5. The method of claim 1, wherein the part of the plurality of lamellas is connected via at least one connection element, to at least one other lamella of the plurality of lamellas, and wherein the plurality of lamellas are aligned by a controlled movement of the at least one connection element.

6. The method of claim 2, wherein the plurality of lamellas are aligned by a translation of each respective lamella of the part of the plurality of lamellas at right angles to the straight line running through the respective lamella in parallel to the other of the plurality of lamellas.

7. The method of claim 2, wherein the aligning of the plurality of lamellas is set by a movement of each respective lamella of the part of the plurality of lamellas, independently of the movement of the other of the plurality of lamellas.

8. The method of claim 2, wherein the part of the plurality of lamellas is connected via at least one connection element, to at least one other lamella of the plurality of lamellas, and wherein the plurality of lamellas are aligned by a controlled movement of the at least one connection element.

9. A non-transitory computer readable medium, storing program for, when executed by at least one processor, perform the method of claim 1.

10. An apparatus for changing a spatial intensity distribution of an x-ray beam, comprising:
a form filter, introduceable into a beam path of the x-ray beam generated by an x-ray source, the form filter including a holder apparatus, a plurality of lamellas being arranged in the holder, wherein each respective lamella of the plurality of lamellas includes at least one straight line running through the respective lamella in parallel to the other of the plurality of lamellas and wherein the plurality of lamellas are alignable relative to the beam path by a controlled movement of at least a part of the plurality of lamellas relative to other of the plurality of lamellas; and
a controller, embodied to control the controlled movement of the part of the plurality of lamellas, to change the spatial intensity distribution of the x-ray beam.

11. The apparatus of claim 10, wherein the holder apparatus includes a plurality of pairs of mounting points arranged on opposite sides and wherein each respective lamella of the part of the plurality of lamellas is arranged rotatably between mounting points of a pair of mounting points, of the plurality of pairs of mounting points.

12. The apparatus of claim 10, wherein the holder apparatus includes a pair of guide rails on opposite sides of the holder and wherein each respective lamella of the part of the plurality of lamellas, is arranged via guidance pins in the pair of guide rails and is arranged movably in parallel to the pair of guide rails.

13. The apparatus of claim 10, wherein at least one connection element is arranged between the holder apparatus and each respective lamella of the part of the plurality of lamellas, and wherein the connection element includes at least one actuator, embodied to move the respective lamella, connected to the at least one actuator, in a controlled manner.

14. The apparatus of claim 10, wherein each respective lamella of the part of the plurality of lamellas is connected by at least one connection element to at least one other lamella of the plurality of lamellas, and wherein the at least one connection element includes at least one actuator, embodied to move the lamellas connected to the at least on actuator in a controlled manner.

15. The apparatus of claim 14, wherein the at least one connection element including the at least one actuator, is further connected to the holder apparatus.

16. The apparatus of claim 13, wherein the at least one actuator features electroactive polymers or piezoelectric ceramics.

17. An irradiation arrangement, comprising:
an x-ray source to generate the x-ray beam; and
the apparatus of claim 10,
wherein the apparatus is positioned in a position relative to the x-ray source.

18. A medical imaging apparatus, comprising the irradiation arrangement as claimed in claim 17.

19. The medical imaging apparatus of claim 18, wherein the medical imaging apparatus is a computed tomography device.

20. The apparatus of claim 11, wherein the holder apparatus includes a pair of guide rails on opposite sides of the holder and wherein each respective lamella of the part of the plurality of lamellas, is arranged via guidance pins in the pair of guide rails and is arranged movably in parallel to the pair of guide rails.

21. The apparatus of claim 11, wherein at least one connection element is arranged between the holder apparatus and each respective lamella of the part of the plurality of lamellas, and wherein the connection element includes at least one actuator, embodied to move the respective lamella, connected to the at least one actuator, in a controlled manner.

22. The apparatus of claim 11, wherein each respective lamella of the part of the plurality of lamellas is connected by at least one connection element to at least one other lamella of the plurality of lamellas, and wherein the at least one connection element includes at least one actuator, embodied to move the lamellas connected to the at least one actuator in a controlled manner.

23. The apparatus of claim 21, wherein the at least one connection element including the at least one actuator, is further connected to the holder apparatus.

24. An apparatus for changing a spatial intensity distribution of an x-ray beam, comprising:
a form filter, introduceable into a beam path of the x-ray beam generated by an x-ray source,
wherein the form filter includes a holder apparatus, a plurality of lamellas being arranged in the holder apparatus,
wherein each respective lamella of the plurality of lamellas includes at least one straight line running through the respective lamella in parallel to the other lamellas of the plurality of lamellas and further includes a height profile in a plane defined by the respective lamella, and
wherein the height profile relates to a height of the respective lamella, extending at right angles to the straight line running through the respective lamella, and changes along the straight lines running through the respective lamella; and
a controller, to at least one of control a controlled movement of the form filter relative to the x-ray source and control a controlled movement of lamellas of at least a part of the plurality of lamellas, relative to one other of the plurality of lamellas, and to change the spatial intensity distribution of the x-ray beam.

25. A computed tomography device, comprising:
an x-ray source; and
an x-ray detector to interact with the x-ray source, wherein the x-ray source and the x-ray detector are arranged rotatably about a system axis located between the x-ray source and the x-ray detector; and
the apparatus of claim 24 for changing a spatial intensity distribution of an x-ray beam from the x-ray source, the form filter being arranged between the x-ray source and the system axis.

* * * * *